(12) United States Patent
Guga et al.

(10) Patent No.: US 7,662,635 B2
(45) Date of Patent: Feb. 16, 2010

(54) DEVICE AND METHOD FOR DETECTING METHYLSOTHIOCYANATE

(75) Inventors: Silke Guga, Lübeck (DE); Andreas Mohrmann, Krummesse (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 127 days.

(21) Appl. No.: 11/987,722

(22) Filed: Dec. 4, 2007

(65) Prior Publication Data
US 2008/0138910 A1  Jun. 12, 2008

(30) Foreign Application Priority Data
Dec. 12, 2006  (DE)  .................. 10 2006 058 459

(51) Int. Cl.
G01N 31/22   (2006.01)
G01N 31/00   (2006.01)
B01J 10/00   (2006.01)

(52) U.S. Cl. .................. 436/109; 436/106; 422/83; 422/50

(58) Field of Classification Search .................. 436/109, 436/106; 422/60, 83, 50
See application file for complete search history.

(56) References Cited

U.S. PATENT DOCUMENTS
5,000,920 A * 3/1991 Heckmann et al. ............ 422/60

FOREIGN PATENT DOCUMENTS
DE          285 196          12/1990

OTHER PUBLICATIONS

M.G. Ashley et al.; "The Action of Metham-sodium in Soil. I.-Development of an Analytical Method for the Determination of Methyl Isothiocyanate Residues in Soil", Journal of the Science of Food and Agriculture, 1963, vol. 14, Issue 3, pp. 148-153.
G.A. Lloyd: "The Elimination of Methyl Isothiocyanate From Soil After Treatment With Metham-sodium", Journal of the Science of Food and Agriculture, 1962, vol. 13, Issue 6, pp. 309-315.
German Office Action dated Apr. 8, 2008 issued in counterpart German Application 10 2006 058 459.7-52.

* cited by examiner

*Primary Examiner*—Walter D Griffin
*Assistant Examiner*—Christine T Mui
(74) *Attorney, Agent, or Firm*—Nixon & Vanderhye P.C.

(57) ABSTRACT

A device and method in which the gas specimen to be investigated is exposed to one or more indicators for qualitative or quantitative detection of methylisothiocyanate, characterized in that at least one indicator is palladium sulfate.

20 Claims, 1 Drawing Sheet

DEVICE AND METHOD FOR DETECTING METHYLSOTHIOCYANATE

CROSS-REFERENCES TO RELATED APPLICATIONS

This application is based on and incorporates herein by reference German Patent Application No. DE 10 2006 058459.7 filed on Dec. 12, 2006.

BACKGROUND OF THE INVENTION

The present invention relates to a method for detecting methylisothiocyanate and to a device for performing the method.

It is often necessary for soil used in agriculture to be fumigated before the next sowing or replanting, for instance by treatment with a fungicide or nematicide. For instance, methylisothiocyanate (MITC) is used to prepare soils both in greenhouses and on open land for the cultivation of vegetables.

When Dazomet is used, methylisothiocyanate is released slowly through the moisture of the soil. MITC is the actual biologically effective agent in this case. The use of metam-sodium (sodium-M-methyldithiocarbamate) as a soil fumigant is also known. Metam-sodium likewise releases MITC as the actual active ingredient.

MITC is a solid at room temperature (melting point 32 to 38° C.) and evaporates slowly and in the process destroys animal pests, fungi, and plants in the soil, so that useful plants, especially vegetables, can germinate and grow without competition. MITC is toxic both to humans and to the useful plants. It is therefore important to protect humans; moreover, the soil must be free of MITC before sowing.

After each use of a soil decontaminant, a certain waiting period must be observed until resowing or replanting of useful and cultivated plants, in order to assure that the soil decontaminant has decomposed extensively enough that there is no need to fear adverse effects on the resowing or replanting. For the farmer, it is of decisive importance to obtain a reliable statement about the length of the waiting period.

The detection of isothiocyanates with inorganic reagents is known per se. For instance, former East German Patent Disclosure DD 285 196 describes a test paper for detecting isocyanates and isothiocyanates, which comprises a paper that is saturated with pyridinium salts. For detecting the aforementioned substances, the test paper is put into contact with the substance to be tested, and then, by vapor deposition of ammonia, an intensive yellowish-orange to orange-red/brown coloration develops.

The known detection methods, however, have proved to be insensitive and/or too expensive in practice.

BRIEF DESCRIPTION OF THE INVENTION

It is therefore the object, among others, of the present invention to make an easily performed method available for determining methylisothiocyanate for ambient air, in particular close to the ground and especially preferably for interiors, as in greenhouses, for instance, which makes it possible to determine the quantity of methylisothiocyanate present simply, reliably, and with the requisite sensitivity.

The method for detection is needed especially in order to ascertain whether it is safe to enter greenhouses, for instance, without protecting equipment like gas masks. By means of soil air analysis (analysis of air in the soil to measure substances which are outgased by the soil), it is also possible to ascertain whether the soil tested is free of MITC.

Surprisingly, it has now been discovered that this object is attained using a detection reagent, in particular a colorimetric indicator, which operates on the basis of palladium sulfate in an acidic environment, preferably sulfuric acid. The detection reagent forms the indication layer, possibly together with a substrate and optionally other substances. The indication layer is preferably part of a transparent glass test tube.

DETAILED DESCRIPTION OF THE INVENTION

Figure 1:
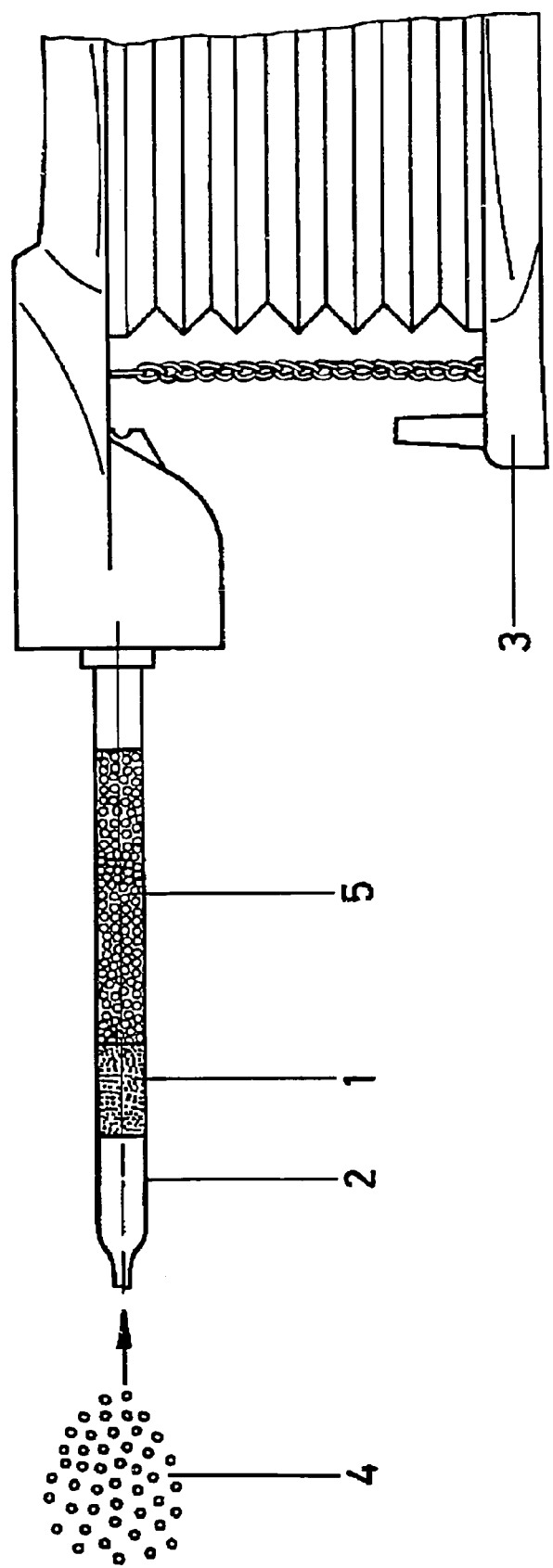
FIG. 1 is a schematic illustration of an example embodiment of a device according to the invention.

As mentioned above, the present invention provides an easily performed method for determining methylisothiocyanate for ambient air, in particular close to the ground and especially preferably for interiors, as in greenhouses, for instance. The invention makes it possible to determine the quantity of methylisothiocyanate present simply, reliably, and with the requisite sensitivity using a detection reagent, in particular a colorimetric indicator, which operates on the basis of palladium sulfate in an acidic environment, preferably sulfuric acid. The detection reagent forms the indication layer, possibly together with a substrate and optionally other substances. The indication layer is preferably part of a transparent glass test tube 2.

The detection reagent is reduced by MITC (presumably to palladium). The result is a color change from yellow to brownish gray. The palladium sulfate is preferably applied to an inert substrate.

To make the measurement as independent as possible of humidity, the indication layer 5 may also be preceded by a dry layer 1, for instance comprising calcium chloride, optionally also on an inert substrate. The dry layer is either placed in a separate tube or in the same tube as the indication layer.

With this test tube, MITC can be measured in the desired concentration ranges quickly, economically, and on-site. With the aid of the method of the invention, it is successfully possible to detect MITC in the ambient air in the range from 0.1 to 100 ppm, and in particular 0.2 to 10 ppm (ppm=mL/m$^3$ or mL/1000 L). The substrate material is preferably a granular material and may for instance be silica gel or quartz glass grit.

Atmospheric MITC can thus be determined quantitatively as well by the intake of a defined gas volume by the test tube.

The test tube 2 preferably has two tips that can be broken off. The test tube includes an indication layer 5 that contains the aforementioned indicator or the detection reagent, and the test tube is optionally also provided with a color scale or measuring scale, so that the concentration of MITC can be determined from the progression of the color trace (moving color front/discoloration of the tube). When the tips have been broken off, a defined quantity of gas 4 can flow through the test tube, for instance by means of a hand pump 3 mounted on the end of the tube.

In terms of the flow direction, there is preferably first a preliminary layer 1 and downstream of it an indication layer 5. The two layers may be separated from one another by an intermediate layer that comprises one or more gas-permeable retainer elements, e.g. an element made from ceramic (or other materials) which fixes (or mounts) the layers in the glass tube. The preliminary layer 1 contains the drying agent, for instance between at least two retainer elements, approximately in the form of a quartz glass grit layer, a glass frit base, or a spun-glass layer. The retainer elements have the function of preventing the preliminary layer and indication layer from trickling through the retainer elements.

In this embodiment, the test tube has a separate preliminary layer 1 containing the drying agent and optionally a suitable trap, e.g. filter layer, for binding interfering substances. The quantity of the gas sample 4 flows through the preliminary layer and leaves the preliminary layer in the form of an (essentially) dried gas, freed of interfering substances if applicable, and flows toward the indication layer 5 containing the indicator.

The preliminary layer may also be part of a separate tube that is connected to the indicator tube, for instance only shortly before the measurement. In this embodiment, a preliminary tube is connected upstream of the actual test tube. The tubes are connectable to one another or communicate with one another for instance through a hose.

If desired, the preliminary layer and indication layer may be provided with a valve element that opens only during the flow through the tube. In an expedient feature of the invention, the valve element may comprise a spring-loaded cup valve or ball valve. This valve then functions in a simple way as a check valve.

The indication layer may be produced for instance by dissolving the palladium sulfate in sulfuric acid and applying it to quartz glass as a substrate. Small quantities (up to approximately 0.1 ml of the solution on 100 g of quartz glass) become uniformly distributed on the substrate, and the preparation remains pourable.

It has been found that nitric acid in the presence of sulfuric acid, where the nitric acid is used in minimal quantities compared to the sulfuric acid, improves the storage stability of the indicator, among other factors.

EXPERIMENTAL EXAMPLE

The production of a substrated indicator is done as follows: A $PdSO_4$ solution containing 0.8 g $PdSO_4$, 7.5 ml water and 2.5 ml $H_2SO_4$ and 1 ml of 1% $HNO_3$ was prepared. As the substrate, 200 g of quartz glass grit was used, which was mixed with 100 µl of the above solution for 30 minutes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A device adapted to be put in contact with a gas specimen to detect methylisothiocyanate, the device comprising a main body with a surface having at least one indicator for qualitative or quantitative determination of methylisothiocyanate disposed thereon, wherein at least one said indicator is palladium sulfate, and the indicator experiences a color change when it is exposed to a gas specimen containing methylisothiocyanate.

2. The device as defined by claim 1, wherein the at least one indicator includes an indication layer comprising palladium sulfate dissolved in sulfuric acid and applied to a substrate.

3. The device as defined by claim 2, wherein the substrate comprises quartz glass.

4. The device as defined by claim 2, wherein the indication layer further comprises nitric acid, whereby a storage stability of the indicator is improved.

5. The device as defined by claim 1, wherein the indicator is applied to the surface in the form of a pourable solid.

6. The device as defined by claim 5, wherein the indicator includes an indication layer comprising palladium sulfate dissolved in sulfuric acid and applied to a substrate.

7. The device as defined by claim 1, wherein the main body is tubular, whereby the gas specimen flows through it.

8. The device as defined by claim 7, wherein the main body is a transparent test tube and the surface on which the indicator is disposed is an inner surface of the transparent test tube.

9. The device as defined by claim 1, further comprising a drying layer applied to the surface of the main body.

10. The device as defined by claim 9, wherein the drying layer comprises calcium chloride.

11. The device as defined by claim 7, further comprising a drying layer disposed in a first tube and the indication layer is disposed in a second tube in flow communication with the first tube.

12. The device as defined by claim 7, further comprising a hand pump mounted to an end of the tubular main body.

13. A method for detecting methylisothiocyanate in a gas specimen to be investigated, comprising:
providing a device comprising a main body with a surface having at least one indicator for qualitative or quantitative determination of methylisothiocyanate disposed thereon, wherein at least one said indicator is palladium sulfate, and the indicator experiences a color change when it is exposed to a gas specimen containing methylisothiocyanate;
exposing the at least one indicator to the gas specimen to be investigated; and
determining whether the indicator undergoes a color change to determine whether the gas specimen contains methylisothiocyanate.

14. The method as defined in claim 13, wherein the indicator comprises palladium sulfate dissolved in sulfuric acid.

15. The method as defined in claim 14, wherein the indicator further comprises nitric acid.

16. The method as defined in claim 14, wherein the indicator is applied to a substrate so as to comprise a pourable solid.

17. The method as defined in claim 13, wherein the device comprises a test tube having the indicator disposed as a layer on an inner surface thereof, and wherein said step of exposing comprises conducting the gas specimen through the test tube.

18. The method as defined in claim 17, wherein the indicator layer is formed by dissolving palladium sulfate in sulfuric acid and applying it to a substrate whereby the preparation remains pourable, and pouring the preparation onto the surface to define an indicator layer.

19. The method as defined in claim 17, wherein the test tube has a scale for quantitative or semi-quantitative analysis of the methylisothiocyanate.

20. The method as defined in claim 17, wherein a defined quantity of the gas specimen is passed through the test tube by means of a hand pump, so as to be exposed to the indicator, the hand pump being placed on an end of the test tube.

* * * * *